United States Patent [19]
Konwitz

[11] Patent Number: 5,638,483
[45] Date of Patent: Jun. 10, 1997

[54] SIDE-EMITTING OPTICAL FIBERS FOR LASERS WITH ORIENTATION MARKINGS

[75] Inventor: Ellie Konwitz, Ramat Gan, Israel

[73] Assignee: Laser Industries, Ltd., Tel Aviv, Israel

[21] Appl. No.: 647,348

[22] Filed: May 9, 1996

[30] Foreign Application Priority Data

May 9, 1995 [IL] Israel ......................... 113674

[51] Int. Cl.$^6$ ......................................... G02B 6/26
[52] U.S. Cl. .................. 385/901; 385/38; 385/31; 362/32
[58] Field of Search .................. 362/32; 385/901, 385/38, 31, 85, 47

[56] References Cited

U.S. PATENT DOCUMENTS

| | | | |
|---|---|---|---|
| 5,343,543 | 8/1994 | Novak, Jr. et al. | 385/31 |
| 5,428,699 | 6/1995 | Pon | 385/131 |
| 5,430,634 | 7/1995 | Baker et al. | 362/32 |

*Primary Examiner*—John Ngo
*Attorney, Agent, or Firm*—Cobrin Gittes & Samuel

[57] ABSTRACT

A side-emitting optical fiber is provided. The side-emitting optical fiber has a proximal end for receiving radiation, a distal end including a distal tip through which the radiation is emitted in a direction laterally of the longitudinal axis of the fiber via a radiation exit regions at the distal tip, and a visually discernible marking. The visually discernible marking is adjacent to the radiation exit region to enable discerning the location of the radiation exit region as the optical fiber is manipulated by a user. The side-emitting optical fiber is characterized in that the visually discernible marking extends for approximately 180° around the circumference of the fiber, has a visually discernible center located approximately 180° radially from the center of the radiation exit region, and has visually discernible opposed axially-extending edges each of a length having a known predetermined relation to the axial distance between a known predetermined point of the marking and the center of the radiation exit region. The arrangement is such that at least one-half the marking, including its center and one of its axially-extending edges, is viewable to the viewer in all orientations of the fiber where the radiation exit region faces away from the user, and thereby enables the user to visually discern both the radial location and the axial location of the center of the radiation exit region.

23 Claims, 3 Drawing Sheets

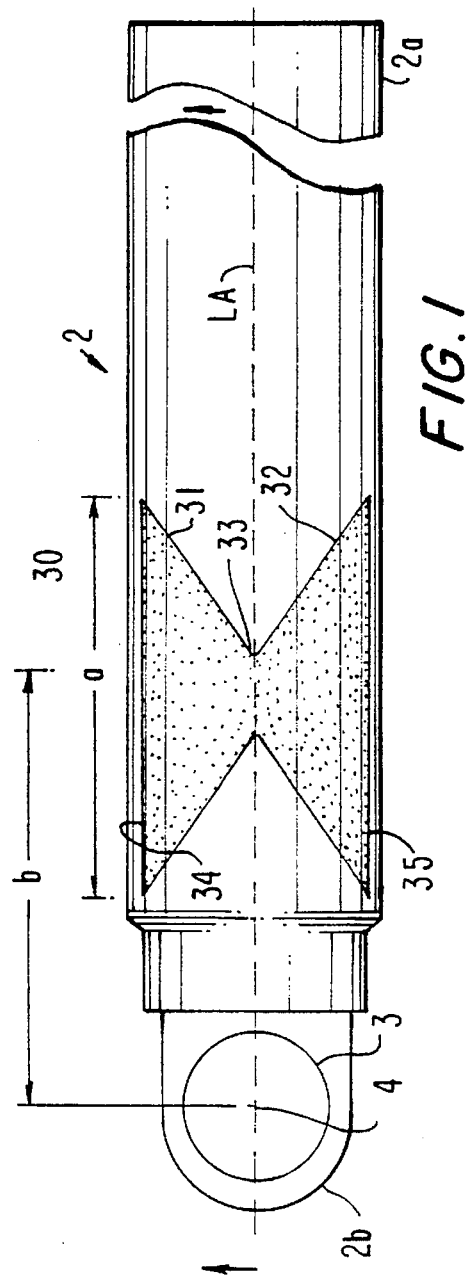
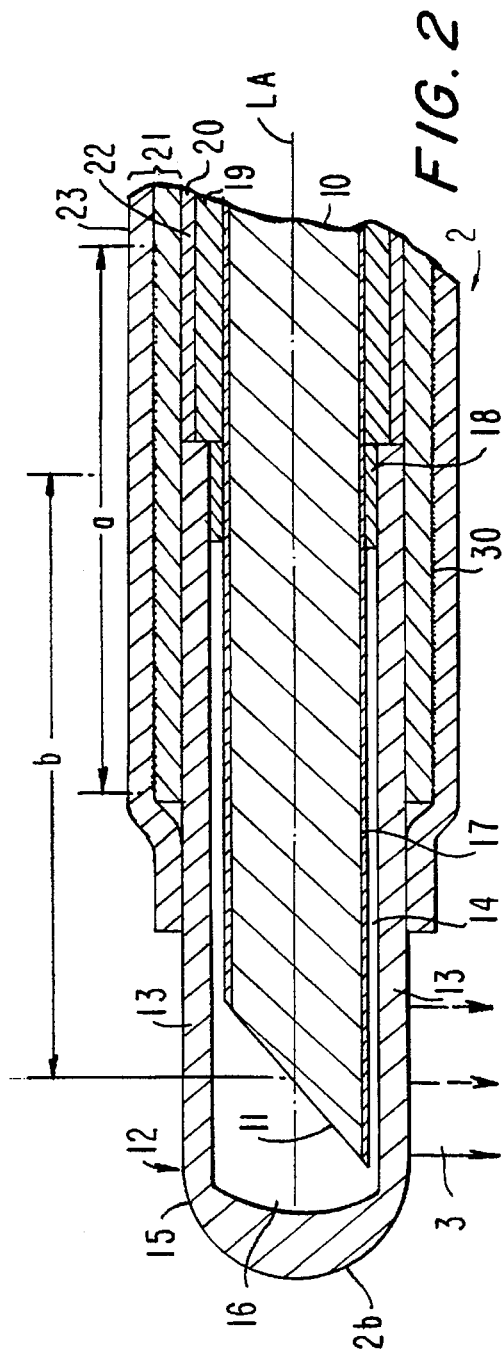

SIDE-EMITTING OPTICAL FIBERS FOR LASERS WITH ORIENTATION MARKINGS

CROSS-REFERENCE TO RELATED APPLICATION

The present application is related to U.S. patent application Ser. No. 08/574,552 (the "'552 application"), entitled "SIDE-EMITTING OPTICAL FIBERS FOR LASERS", filed Dec. 19, 1995, which claims priority of Israeli Application Ser. No. 112087, filed Dec. 20, 1994.

The present invention relates to side-emitting (or side-firing) optical fibers such as are used in laser surgery. The invention is particularly directed to an optical fiber construction having an orientation marking which enables visually discerning the orientation of the optical fiber with respect to the exit region of the laser radiation from the fiber.

Laser apparatus used during examination or surgery commonly includes an optical fiber for directing the laser radiation from the laser to the tissue being examined or treated. When end-firing fibers are used (i.e., those in which the laser radiation is emitted axially of the fiber end), the surgeon can easily discern the direction of the emitted radiation according to the axis of the emitting fiber. However, in side-emitting optical fibers (i.e., those in which the radiation is emitted laterally of the longitudinal axis of the fiber, e.g., 90° or any smaller angle to the longitudinal axis), the radiation exit region from the fiber is obscured by the fiber itself when that region faces away from the surgeon, so that the surgeon cannot readily discern the direction of radiation emisssion when the exit region does not actually face the surgeon.

U.S. Pat. No. 5,343,543 describes one arrangement for enabling a surgeon to discern the direction of radiation emission from a side-fired optical fiber.

An object of the present invention is to provide a side-emitting optical fiber, particularly useful as a side-firing laser fiber.

According to one aspect of the present invention, there is provided a side-emitting optical fiber having a proximal end for receiving radiation, a distal end including a distal tip through which the radiation is emitted in a direction laterally of the longitudinal axis of the fiber via a radiation exit region at the distal tip, and a visually discernible marking adjacent the radiation exit region to enable discerning the location of the radiation exit region as the optical fiber Is manipulated by a user; characterized in that the visually discernible marking: (a) extends for approximately 180° around the circumference of the fiber, (b) has a visually discernible center located approximate 180° radially from the center of the radiation exit region, and (c) has visually discernible opposed axially-extending edges each of a length having a known predetermined relation to the axial distance between a known predetermined point of the marking and the center of the radiation exit region. The arrangement is such that at least one-half of the marking, including its center and one of its axially-extending edges, is viewable to the viewer in all orientations of the fiber where the radiation exit region faces away from the user, and thereby enables the user to visually discern both the radial location and the axial location of the center of the radiation exit region.

As will be described more particularly below, a side-emitting optical fiber constructed in accordance with the foregoing features is particularly useful in surgical procedures, such as in the transurethral treatment of the prostate, since it enables the surgeon to readily discern, both the radial location and the axial location, of the center of the radiation exit region in all positions of the optical fiber facing away from the surgeon as the optical fiber is manipulated by the surgeon. Where the fiber faces the surgeon, the position of the radiation exit region is discernible by the marker beam normally provided in surgical lasers of this type, or by the beam itself or the results produced by the beam if the marker beam is not provided.

Preferably, the known predetermined relation of the above feature (c) is equality, and the known predetermined point is the center of the marking. That is, in such an arrangement as described below, the axial distance of the center of the radiation exit region to the center of the marking is equal to the length of the opposed axially-extending edges of the marking, such that the surgeon, by merely glancing at the marketing, can thereby visually discern both the radial location and the axial location of the center of the radiation exit region. While this is a preferred arrangement, examples of other arrangements which may be used are also described.

In two embodiments of those described below, the marking includes two substantially triangular sections having apices joined together at a juncture which is at the center of the marking, and bases which extend substantially parallel to the longitudinal axis of the fiber. In another described embodiment, the marking is of rectangular configuration and includes a visibly discernible central axis.

According to another aspect of the present invention, there is provided a side-emitting optical fiber having a proximal end for receiving radiation, and a distal end for emitting the radiation in a direction laterally of the longitudinal axis of the fiber via a radiation exit region at the distal end; an outer covering over the optical fiber terminating short of its distal tip; a cap of a heat-resistant radiation-transparent material at the distal tip and enclosing the radiation-exit region; and a visually discernible marking covered by the outer plastic covering and enabling a user to discern the location of the radiation exit region as the optical fiber is manipulated by the user; the outer plastic covering being transparent, having an index of refraction substantially higher than 1.00, and being bubble-free through the thickness thereof to the marking such that the marking is clearly viewable through the outer plastic sleeve even under small viewing angles.

As will be described more particularly below, such a construction permits the user to readily see the marking and also effectively protects the marking against removal or smudging before, during or after use of the optical fiber.

Further features and advantages of the invention will be apparent from the description below.

The invention is herein described, by way of example only, with reference to the accompanying drawings, wherein:

FIG. 1 is a plan view illustrating the marking on one type of optical fiber constructed in accordance with the present invention;

FIG. 2 is a longitudinal sectional view along line II—II of FIG. 1, more particularly illustrating the construction of the optical fiber;

Figure 6:
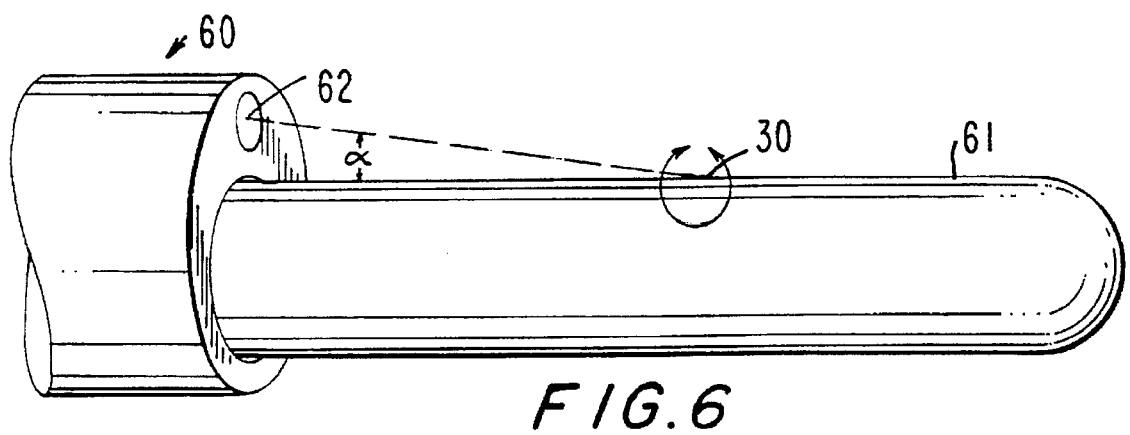

and FIG. 6 illustrates a cystoscope including an optical fiber constructed in accordance with the present invention.

The optical fiber illustrated in FIGS. 1 and 2 is adapted for use particularly in a cystoscope as illustrated in FIG. 6, but may be used in many other applications for the examination, treatment or removal of tissue within a body cavity by laser radiation, or in many non-medical applications. The optical fiber, therein generally designated 2, has a proximal end 2a to be coupled to a laser (not shown) for receiving the laser radiation, and a distal end 2b for emitting the radiation in a direction laterally of the longitudinal axis LA of the optical fiber via a radiation exit region 3, having a center 4, at the distal end of the fiber.

Fiber 2 includes an elongated fiber core 10 which terminates at its distal end 2b in an angled reflecting surface 11 enclosed by a cap 12 at the distal tip of the fiber. Cap 12 includes a cylindrical wall 13 of slightly larger inner diameter than the outer diameter of the core 10 to provide an annular air space 14; such an air space, however, may be omitted. Cap 12 further includes a semi-spherical end wall 15 which is axially spaced from the angled reflecting surface 11 of the core 10 to provide an axial air space 16.

The core 10 is covered on its outer surface by a cladding 17 for its complete length up to the angled reflecting surface 11, to thereby confine the radiation to that angled surface. If desired, an adhesive 18 may be applied between cylindrical wall 13 of the distal cap 12 and the core cladding 17. The angled reflecting surface 11 of the core 10 is effective to reflect the radiation laterally of the longitudinal axis LA of the fiber and through the cylindrical wall 13 of the cap 12, to exit via region 3, as shown in FIG. 2. For this purpose, cap 12 is made of a radiation-transparent, heat-resistant material, such as fused silica or glass. The semi-spherical end wall 15 of the cap facilitates the insertion of the optical fiber into the cavity, channel or tissue to be treated or examined by the laser radiation.

The fiber 2 further includes a plastic buffer layer 19 over the cladding 17 protecting the fiber core 10, and a plastic jacket 20 over the buffer layer 19. Both layers 19 and 20 terminate at the distal cap 12. The distal end of the fiber includes an outer plastic covering, generally designated 21, which partly covers the distal cap 12 but terminates just short of the angled reflecting surface 11 so as not to receive the radiation reflected laterally of the fiber by that surface.

Cover 21 includes an internal sleeve 22 which is heat-shrunk over layers 19 and 20 and the adjoining portion of the distal cap 12, and an outer sleeve 23 which is transparent and also heat-shrunk over sleeve 22 and the distal cap 12.

A marking, generally designated 30, is printed over the outer surface of sleeve 22 after it has been heat-shrunk onto the fiber, and before the outer sleeve 23 has been applied. Marking 30 has the following features:

(a) extends for approximately 180° around the circumference of the fiber, (b) has a visually discernible center located approximately 180° radially from the center of said radiation exit region, and (c) has visually discernible opposed axially-extending edges each of a length having a known predetermined relation to the axial distance between a known predetermined point of the marking and the center of the radiation exit region.

As will be described more particularly below, when the marking has these features, at least one-half of the marking, which includes its center and one of the axially-extending edges, is viewable to the viewer in all orientations of the optical fiber where the radiation exit region faces away from the user, and thereby enables the user to discern both the radial location and the axial location of the center of the radiation exit region.

FIGS. 1 and 2 illustrate one example of such a marking 30, and FIGS. 3a–3e illustrate how such a marking enables the user to discern the radiation exit region.

As shown particularly in FIG. 1, marking 30 consists of two similar, substantially triangular sections 31, 32, having apices joined together at a juncture 33 and relatively straight bases 34, 35, extending substantially parallel to the longitudinal axis LA of the fiber. The two triangular sections 31, 32, each extend approximately 90° of the circumference of the fiber, so that the two sections together extend approximately 180°, preferably just slightly less than 180°. The juncture 33 of the two apices is located at the center of the marking and approximately 180° circumferentially from (i.e., on the opposite side of) the center 4 of the radiation exit region 3.

In FIGS. 1 and 2, the axial length of each of the two bases 34, 35, is indicated as "a"; and the axial distance between the center of the marking 30 (i.e., the juncture 33) and the center of the angled reflecting surface 11 (defining the exit region 3 of the laser radiation), is indicated as "b". In this example, a=b.

Thus, by observing the marking 30, the surgeon is able to discern both the axial location, and the radial location, of the center 4 of the laser radiation exit region 3 irrespective of the position of the fiber where this exit region faces away from the user. This will be apparent from FIGS. 3a–3e.

Figure 3A:
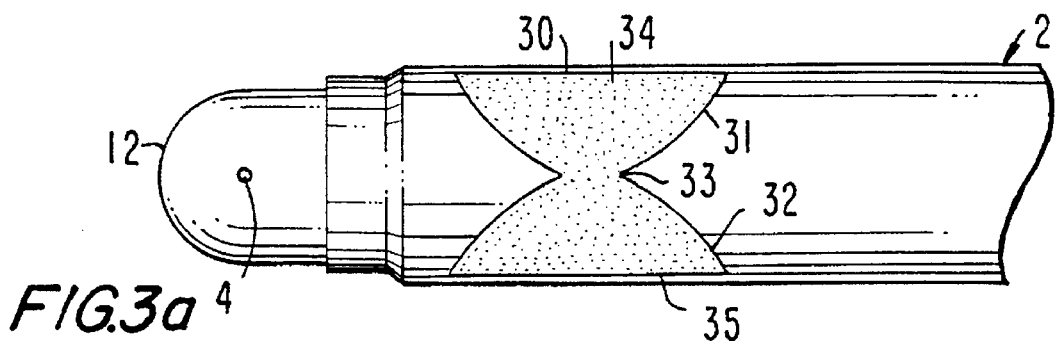
FIGS. 3a–3e illustrate various orientations of the optical fiber of FIGS. 1 and 2 and the manner in which the marking enables the user to discern the exit region of the laser radiation from the fiber.

FIG. 3a illustrates the condition when both triangular section 31, 32 are seen by the observer. In this case, the observer is informed that the center 4 of the radiation exit region 3 is directly on the opposite side of the fiber, in alignment with the juncture 33 of the apices of the two triangular sections 31, 32, and is axially spaced from the center of juncture 33 by the length of each of the bases 34, 35 (i.e., a=b) as described above with respect to FIG. 1.

Figure 3B:
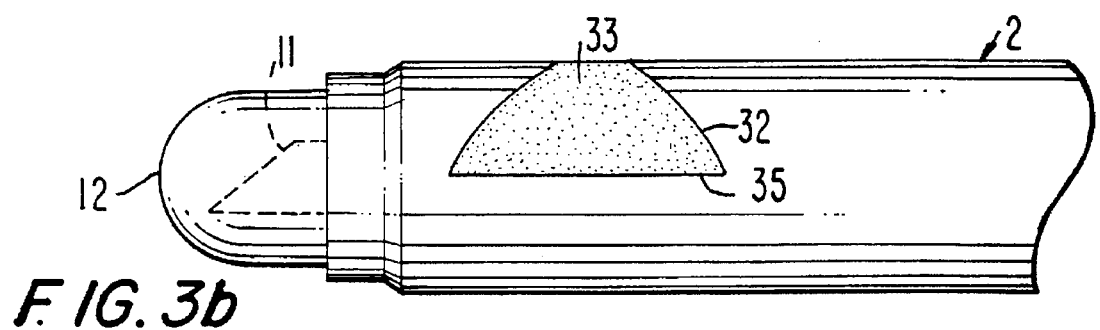
Figure 3C:
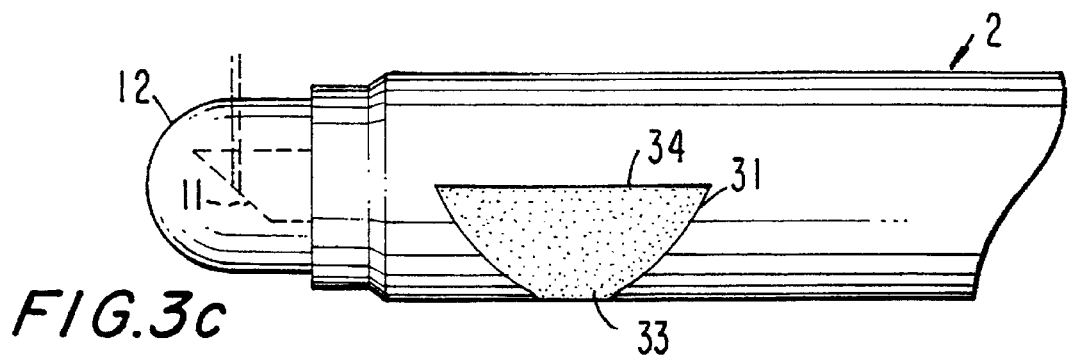
Figure 3D:
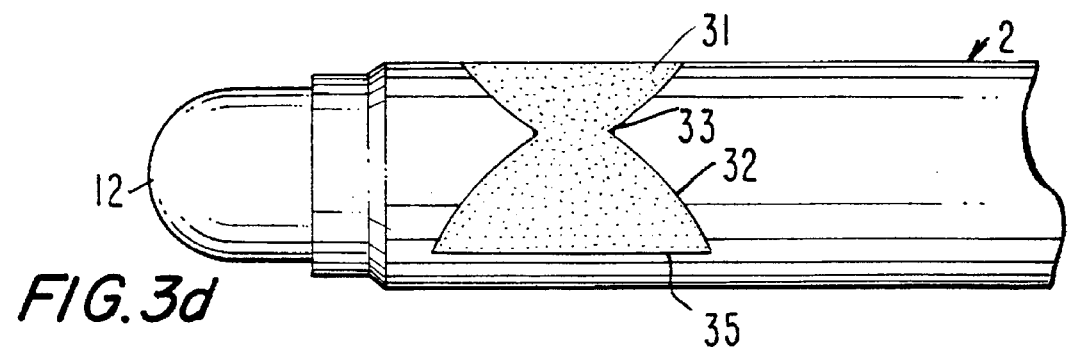

FIG. 3b illustrates the condition of the fiber when only one triangular section 32 is seen by the observer, in which case the observer can still see the juncture 33 between the apices of the two triangular sections, and also the base 35, so that the observer can again discern both the axial and radial location of the center 4 of the radiation exit region 3. FIG. 3c illustrates a similar condition as in FIG. 3b, but when the fiber is oriented so that the other triangular section 31 is observed. FIG. 3d illustrates the orientation of the fiber when one triangular section 32 is observed and a part of the second triangular section 31; wherein it will be seen that the juncture 33 of the two apices is observable and also the length of the base 35.

Figure 3E:
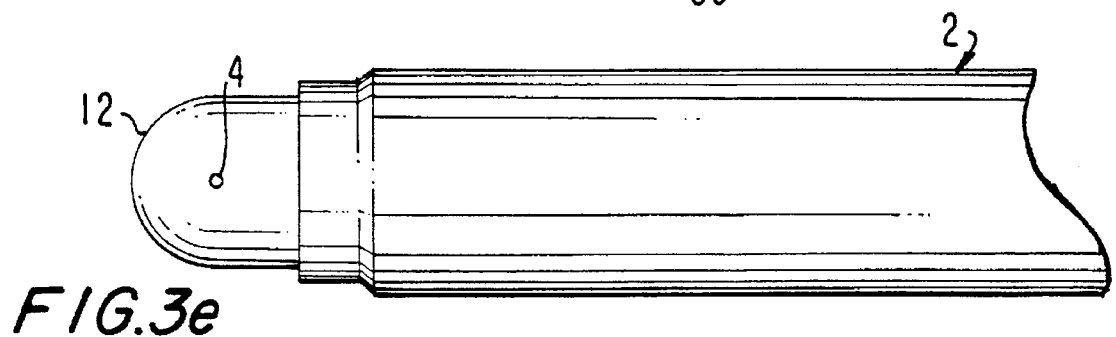

FIG. 3e illustrates the situation when no part of marking 30 is discernible by the observer, i.e., when the fiber is oriented so that marking 30 is exactly facing away from the observer. In this case, the center 4 of the radiation exit region 3 faces the observer, so that the observer can directly see the visual marker beam usually provided with a laser operating beam of the invisible type. If no marker beam is provided, the user will be able to see the laser beam itself (if a visible one) or the results produced by the laser beam when impinging tissue. The above condition also applies when the fiber is oriented less than 90° in either direction from the position illustrated in FIG. 3e, wherein either the juncture 33, or neither of the bases 34, 35, would be observable.

Each of the two triangular sections 31, 32 of marking 30 is substantially in the configuration of an isosceles triangle, i.e., one having two equal sides (these being the two sides on opposite sides of the bases 34, 35).

Figure 4:
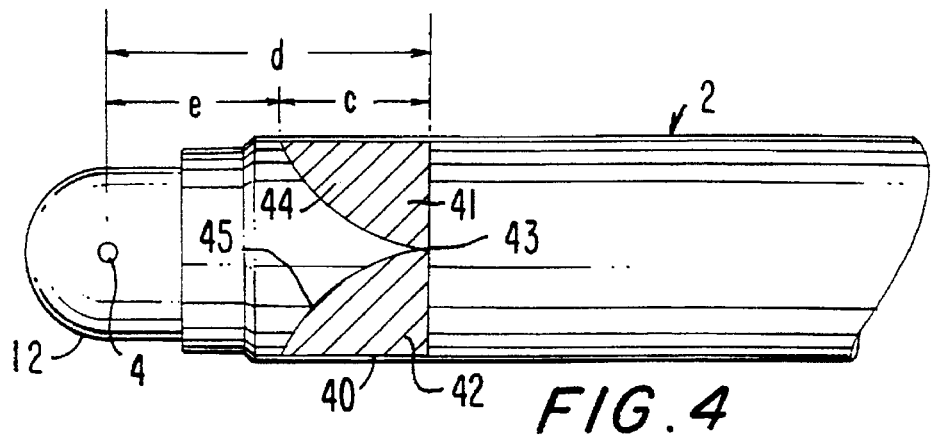
FIGS. 4 and 5 are views similar to that of FIG. 1 but illustrating other types of marking that may be used.

FIG. 4 illustrates a variation wherein marking 40 includes two similar, substantially triangular sections 41, 42 each of a right-triangular configuration. Such a marking also defines a juncture 43 between the apices of the two triangular sections 41, 42, and bases 44, 45 extending substantially parallel to the longitudinal axis of the fiber. In this case, the length of each of the bases 44, 45 is "c", the distance between the marking center (juncture 43) and the center 4 of the radiation exit region 3 is indicated as "d", and the distance between the distal end of the base (44 or 45) and the center 4 of the radiation exit region is indicated as "e". Thus, the observer could discern the axial location of the center 4 of the radiation exit region 3 by reference to dimension "e" (wherein c=e), or by reference to the center of the marking, i.e., the juncture 43 (wherein d=c+e=2c). In this case, the radial location of the center of the radiation exit region would be 180° from the center of the marking (juncture 43) as described above with respect to FIGS. 1 and 2.

Figure 5:
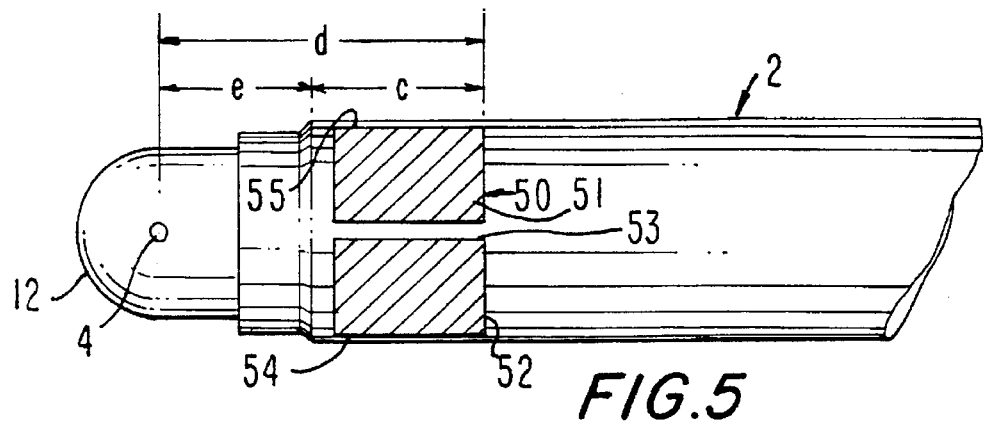

FIG. 5 illustrates another configuration of marking that may be used to enable the surgeon to discern the axial and radial location of the center of the radiation exit region. The marking shown in FIG. 5, and therein generally designated 50, is of rectangular configuration and extends approximately 180° of the circumference of the fiber, preferably just slightly less than 180°. It includes a discernible central axis 51 dividing the marking into two similar rectangular sections 52, 53, each having a base 54, 55 of known axial length "a", with the center 4 of the radiation exit region 3 spaced from the end of each base by a distance "b" equal to "a". Thus, both the axial location, and the radial location, of the center 4 of the radiation exit region 3 are discernible in the same manner as described above.

FIG. 6 illustrates a cystoscope, generally designated 60, for insertion through the urethra of a patient in order to treat the prostate by means of laser radiation side-emitted from an optical fiber 61, which may be of any of the constructions described above. Cystoscope 60 includes an optical channel 62 to permit viewing the optical fiber 61, particularly the marking (e.g., 30, 40 or 50 described above), to enable the surgeon to discern the radial and axial location of the center 4 of the radiation exit region 3 in the manner described above. The angle α, defining the viewing angle between the optical channnel 62 and the outer surface of the fiber 61, is generally very small, which will therefore make it difficult to view the marking, designated 30 in FIG. 6, via the outer transparent sleeve 23 (FIG. 2). For this reason, sleeve 23 should be applied in a manner which does not produce any air bubbles between the sleeve and the marking 30; in addition, the index of the refraction of all the layers from the outer surface of sleeve 23 to the marking should be substantially greater than 1 (the index of refraction of air), preferably substantially greater than 1.33 (the index of refraction of water).

One manner of accomplishing this is to heat the outer sleeve 23 (FIG. 2), before it is applied over the marking (30) on the inner sleeve 22 in order to soften its inner face, and then to heat-shrink it onto the inner sleeve to thereby bond the two sleeves together in a substantially bubble-free manner between the two sleeves.

Instead of using heat, a solvent could be applied to the inner face of the outer sleeve 23 in order to soften it, and thereby to produce a bubble-free bond between it and the inner sleeve 22 when the outer sleeve 23 is heat-shrunk onto the inner sleeve with the marking between the two sleeves.

Another technique for producing a bubble-free condition between the marking and the outer sleeve 23 would be to apply the marking to the outer face of sleeve 23, invert the sleeve, and then heat-shrink it onto the inner sleeve 22. A further possible technique would be to print the marking directly on the inner face of the sleeve, e.g., by printing on a mandrel and inserting the mandrel into the sleeve to transfer the printing to the inner face of the sleeve, and then heat-shrinking the sleeve onto the inner sleeve 22.

Any of the foregoing techniques may also be used without the inner sleeve 22, i.e., with the outer sleeve heat-shrunk directly onto the jacket 20 of the fiber, with the marking applied either to the outer face of the fiber jacket or to the inner face of the outer sleeve.

Following are examples of various materials that may be used in the construction of the illustrated optical fiber: fiber core 10, glass; fiber cladding 17, glass or silicone rubber; buffer layer 19, silicone rubber; jacket 20 and/or the inner sleeve 22, nylon, polyvinylchloride or "Teflon" (™); and the outer sleeve 23, a heat-shrinkable polyester, nylon or "Teflon" (™).

While the invention has been described with respect to several preferred embodiments, it will be appreciated that these are set forth merely for purposes of example, and that many other variations, modifications and applications of the invention may be made.

I claim:

1. A side-emitting optical fiber having a proximal end for receiving radiation, a distal end including a distal tip through which the radiation is emitted in a direction laterally of the longitudinal axis of the fiber via a radiation exit regions at said distal tip, and a visually discernible marking adjacent said radiation exit region to enable discerning the location of the radiation exit region as the optical fiber is manipulated by a user, characterized in that said visually discernible marking:

a. extends for approximately 180° around the circumference of the fiber, b. has a visually discernible center located approximately 180° radially from the center of said radiation exit region, and c. has visually discernible opposed axially-extending edges each of a length having a known predetermined relation to the axial distance between a known predetermined point of the marking and the center of the radiation exit region, such that a at least one-half the marking, including said center and one of said axially-extending edges, is viewable to the viewer in all orientations of the fiber where the radiation exit region faces away from the user, and thereby enables the user to visually discern both the radial location and the axial location of the center of the radiation exit region.

2. The optical fiber according to claim 1, wherein known predetermined relation is equality.

3. The optical fiber according to claim 1, wherein said known predetermined point is said center of the marking.

4. The optical fiber according to claim 1, wherein said known predetermined point is the end of the viewable axially-extending edge of the marking closest to said radiation exit region.

5. The optical fiber according to claim 1, wherein said marking includes two substantially triangular sections having apices joined together at a juncture which is at said center of the marking, and bases which constitute said opposed axially-extending edges of the marking.

6. The optical fiber according to claim 5, wherein said substantially triangular sections define isosceles triangles.

7. The optical fiber according to claim 5, wherein said substantially triangular sections define right-angled triangles.

8. The optical fiber according to claim 1, wherein said marking is of rectangular configuration having a visibly discernible central axis at said center.

9. The optical fiber according to claim 1, wherein the optical fiber includes an outer plastic covering terminating short of its distal tip, and a cap of a heat-resistant, radiation-transparent material at the distal tip enclosing said radiation exit region of the fiber, said marking being printed under said outer plastic covering so as to be protected thereby, said outer plastic covering being transparent, having an index of refraction substantially higher than 1.00, and being bubble-free through the thickness thereof to the marking such that said marking is clearly visible through said outer plastic covering even under small viewing angles.

10. The optical fiber according to claim 9, wherein said outer plastic covering includes an inner layer on which said marking is applied, and an outer transparent sleeve bonded to said inner layer with a bubble-free interface between said inner layer and said outer transparent sleeve.

11. The optical fiber according to claim 9, wherein said marking is printed on the outer surface of the optical fiber, and said outer plastic covering includes a transparent sleeve bonded with a bubble-free interface to the outer surface of the optical fiber.

12. The optical fiber according to claim 10, wherein said outer transparent sleeve is of a heat-shrinkable plastic material and is bonded by an adhesive having an index of refraction substantially greater than 1.00.

13. The optical fiber according to claim 10, wherein said outer transparent sleeve is of a heat-shrinkable plastic material and is bonded by a solvent applied to the inner surface of said outer sleeve before the outer sleeve is heat-shrunk onto the optical fiber.

14. The optical fiber according to claim 10, wherein the marking is applied to the outer surface of the outer transparent sleeve, which sleeve is of heat-shrinkable material and is inverted when applied to the optical fiber.

15. The optical fiber according to claim 9, wherein the index of refraction of said outer plastic covering is greater than 1.33.

16. A side-emitting optical fiber having a proximal end for receiving radiation, and a distal end for emitting the radiation in a direction laterally of the longitudinal axis of the fiber via a radiation exit region at said distal end; said side-emitting optical fiber comprising:

a. an outer covering over the optical fiber terminating short of its distal tip;

b. a cap of a heat-resistant radiation-transparent material at said distal tip and enclosing said radiation-exit region; and c. a visually discernible marking covered by said outer plastic covering and enabling a user to discern the location of said radiation exit region as the optical fiber is manipulated by the user;

said outer plastic covering being transparent, having an index of refraction substantially higher than 1.00, and being bubble-free through the thickness thereof to the marking such that said marking is clearly viewable through said outer plastic covering even under small viewing angles.

17. The optical fiber according to claim 16, wherein said outer plastic covering includes an inner layer on which said marking is applied, and an outer transparent sleeve bonded to said inner layer with a bubble-free interface between said inner layer and said outer transparent sleeve.

18. The optical fiber according to claim 16, wherein said marking is printed on the outer surface of the optical fiber, and said outer plastic covering includes a transparent sleeve bonded with a bubble-free interface to the outer surface of the optical fiber.

19. The optical fiber according to claim 17, wherein said outer transparent sleeve is of a heat-shrinkable plastic material and is bonded by an adhesive having an index of refraction substantially greater than 1.00.

20. The optical fiber according to claim 17, wherein said outer transparent sleeve is of a heat-shrinkable plastic material and is bonded by a solvent applied to the inner surface of said outer sleeve before the outer sleeve is heat-shrunk onto the optical fiber.

21. The optical fiber according to claim 17, wherein the marking is applied to the outer surface of the outer transparent sleeve, which sleeve is of heat-shrinkable material and is inverted when applied to the optical fiber.

22. The optical fiber according to claim 16, wherein the index of refraction of said outer plastic covering is greater than 1.33.

23. The optical fiber according to claim 16, wherein said visually discernible marking:

a. extends for approximately 180° around the circumference of the fiber, b. has a visually discernible center located approximately 180° radially from the center of said radiation exit region, and c. has visually discernible opposed axially-extending edges each of a length having a known predetermined relation to the axial distance between a known predetermined point to the marking and the center of the radiation exit region, such that at least one-half of the marking, including said center and one of said axially-extending edges, is viewable to the viewer in all orientations of the fiber where the radiation exit region faces away from the user, and thereby enables the user to visually discern both the radial location and the axial location of the center of the radiation exit region.

* * * * *